(12) United States Patent
Bagaoisan et al.

(10) Patent No.: US 11,452,520 B2
(45) Date of Patent: *Sep. 27, 2022

(54) SLIDING SUTURE GRASPER

(71) Applicant: TELEFLEX MEDICAL INCORPORATED, Morrisville, NC (US)

(72) Inventors: Celso Bagaoisan, Union City, CA (US); Suresh Pai, Los Altos, CA (US); Brad Labarbera, Ludlow, KY (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 724 days.

This patent is subject to a terminal disclaimer.

(21) Appl. No.: 16/378,544

(22) Filed: Apr. 8, 2019

(65) Prior Publication Data

US 2019/0231347 A1 Aug. 1, 2019

Related U.S. Application Data

(63) Continuation of application No. 15/350,508, filed on Nov. 14, 2016, now Pat. No. 10,251,640, which is a (Continued)

(51) Int. Cl.
| | |
|---|---|
| *A61B 17/04* | (2006.01) |
| *A61B 17/00* | (2006.01) |
| *A61B 17/06* | (2006.01) |
| *A61B 90/00* | (2016.01) |
| *A61B 17/34* | (2006.01) |

(52) U.S. Cl.
CPC ...... *A61B 17/0483* (2013.01); *A61B 17/0469* (2013.01); *A61B 17/0485* (2013.01); *A61B 17/3474* (2013.01); *A61B 2017/00349* (2013.01); *A61B 2017/00353* (2013.01); *A61B 2017/00367* (2013.01); *A61B 2017/061* (2013.01); *A61B 2090/036* (2016.02)

(58) Field of Classification Search
CPC ............ A61B 17/0469; A61B 17/0482; A61B 17/0483; A61B 17/0485; B25B 9/00
USPC .......................................... 294/100; 606/148
See application file for complete search history.

(56) References Cited

U.S. PATENT DOCUMENTS

| | | | |
|---|---|---|---|
| 2,752,625 | A | 7/1956 | Ponsell |
| 5,181,919 | A | 1/1993 | Bergman et al. |

(Continued)

FOREIGN PATENT DOCUMENTS

| | | |
|---|---|---|
| CN | 1084046 A | 3/1994 |
| CN | 1387828 A | 1/2003 |

(Continued)

*Primary Examiner* — Katherine M Shi
(74) *Attorney, Agent, or Firm* — BakerHostetler

(57) ABSTRACT

A device to assist in securing a holding a portion of a suture during an intra-abdominal suturing procedure, the device including an elongated tubular body, a handle, an inner member element, and a push button. The inner member element may include at least one grasping element that expands as the at least one grasping element is extended beyond a distal end of the elongated tubular. The device may include a proximal spring disposed within the push button and abutting against a proximal end of the inner member element to allow the at least one grasping element to retract into the elongated tubular body in a proximal direction.

20 Claims, 6 Drawing Sheets

Related U.S. Application Data continuation of application No. 14/564,345, filed on Dec. 9, 2014, now Pat. No. 9,492,163.

(60) Provisional application No. 61/913,906, filed on Dec. 9, 2013.

(56) References Cited

U.S. PATENT DOCUMENTS

| | | |
|---|---|---|
| 5,816,258 A | 10/1998 | Jervis |
| 5,817,111 A | 10/1998 | Riza |
| 5,921,918 A | 7/1999 | Riza |
| 6,077,277 A | 6/2000 | Mollenauer et al. |
| 6,719,763 B2 | 4/2004 | Chung et al. |
| 7,131,978 B2 | 11/2006 | Sancoff et al. |
| 8,574,245 B2 | 11/2013 | Garrison et al. |
| 2001/0031984 A1 | 10/2001 | Hart |
| 2007/0250112 A1 | 10/2007 | Ravikumar et al. |
| 2010/0191260 A1 | 7/2010 | Mohajer |
| 2013/0218175 A1 | 2/2013 | Auerback et al. |
| 2014/0188138 A1 | 7/2014 | Melscheimer et al. |

FOREIGN PATENT DOCUMENTS

| | | |
|---|---|---|
| CN | 101478923 A | 7/2009 |
| CN | 201320217 Y | 10/2009 |
| CN | 202960665 U | 6/2013 |
| EP | 2233086 A1 | 9/2010 |
| JP | H09135841 A | 5/1997 |
| JP | 2004508070 A | 3/2004 |
| WO | 0178809 A1 | 10/2001 |
| WO | 2006039296 A2 | 4/2006 |
| WO | 2015017554 A1 | 2/2015 |

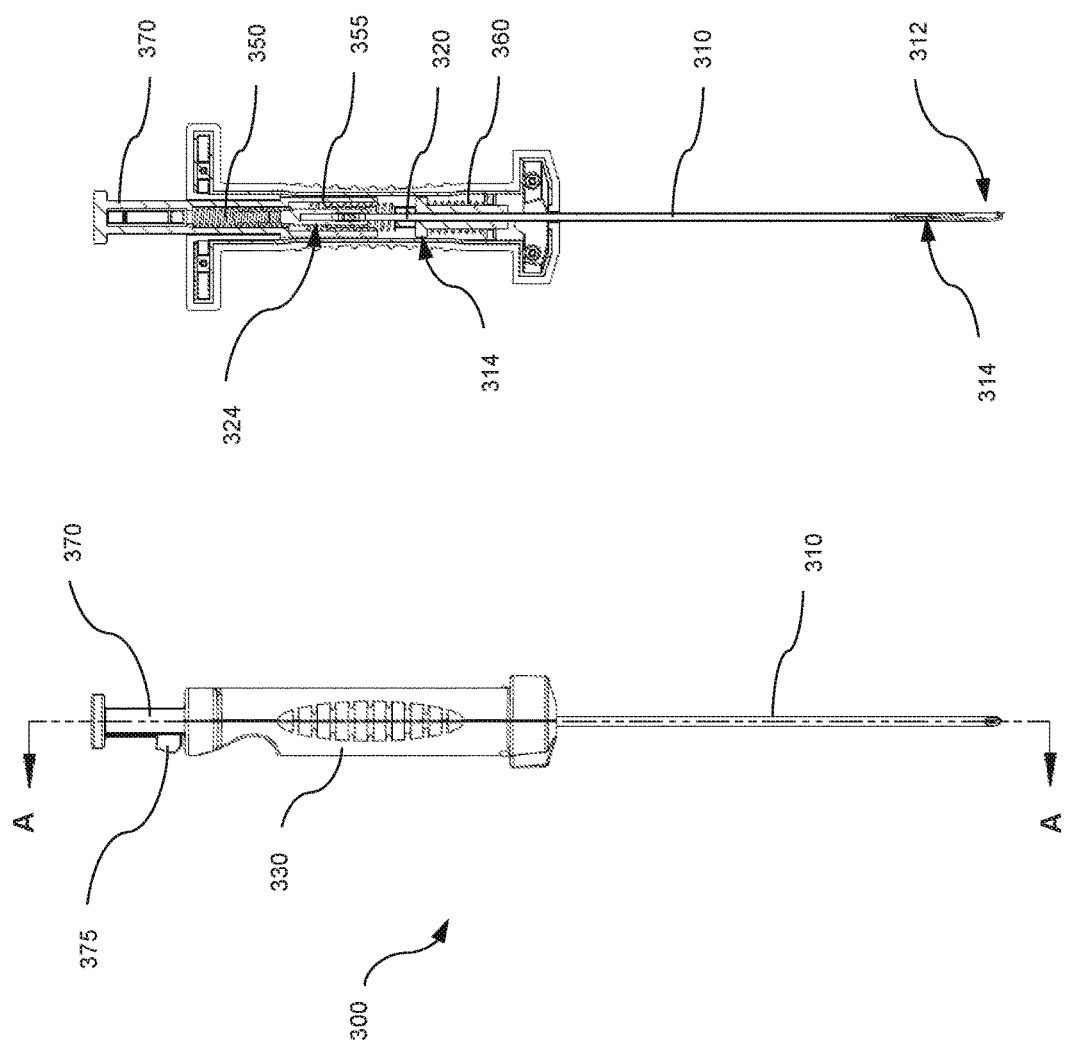

SLIDING SUTURE GRASPER

CROSS-REFERENCE TO RELATED APPLICATION

This patent application is a continuation of U.S. patent application Ser. No. 15/350,508 (filed Nov. 14, 2016 and issued as U.S. Pat. No. 10,251,640), which is a continuation of U.S. patent application Ser. No. 14/564,345 (filed Dec. 9, 2014 and issued as U.S. Pat. No. 9,492,163), which claims priority to U.S. Provisional Patent Application No. 61/913, 906 (filed Dec. 9, 2013), the disclosures of which are incorporated herein by reference in their entireties.

FIELD OF THE INVENTION

The present disclosure relates to tissue closure devices, more particularly to a suture grasper device for securing and holding a portion of a suture during an intraabdominal suturing procedure or the suturing of a puncture wound generated by a surgical trocar or other puncturing devices.

BACKGROUND

Minimally invasive methods for conducting surgery on internal organs, tissues, ligaments and bones use extremely small instruments such as catheters, laparoscopes, and the like. The instruments are introduced using very small incisions, for example on the order of 5 mm to 18 mm in diameter, into which a trocar or other introducing device is placed. The trocars may have a diameter, for example, between 3 mm and 30 mm, with the smaller trocars leaving the opening substantially unchanged. The larger trocars may enlarge the opening. The trocars provide a reliable and fixed opening for introducing and removing various surgical instruments, viewing devices and other instruments used during the surgical procedure.

While the incisions and the trocar opening are quite small by traditional surgical standards, they still require closure after completing the surgical procedure. Surgical closure reduces the possibility of post-surgical infection, postsurgical herniation (for example in abdominal surgeries), subsequent bleeding or other effects. Closure can be accomplished either through manual suturing or suturing instruments used to complete the closure. In either case, suturing is made difficult by the small opening size, for example not only for manipulating the suture but also for visualizing the procedure. Closure is also made more difficult by the need to suture the subcutaneous tissue, for example fascial layers, separate from closure of the overlying skin, and doing so through a very small opening in the skin while also avoiding possible injury or damage to the internal organs during such a procedure.

Conventional closure techniques such as those for closing openings in the abdominal wall pass sutures through the abdominal wall tissue a distance from the original trocar incision. One or more sutures are then tied off to close the subcutaneous layer followed by suitable closure of the skin layer. It has been noted that the distance of the suture location from the original incision opening is important in order to secure a suitable amount of abdominal wall tissue for forming a reliable closure. If the distance is too small, the closure may not be enough to reliably close the opening without later complications.

Tissue closure devices, for example laparoscopic port closure devices, may be introduced into the opening after removal of the trocar device to make easier the suturing of the trocar opening. Various methods and structures may help in closing the opening, but may require a significant number of steps for completing the closure. Some devices may require a significant amount of manual care in suturing the opening and tying off the suture, as well as close visualization for accomplishing the closure. Additionally, some devices have a significant number of components or special devices in order to accomplish the closure, or they may not provide consistent and reliable results even under normal operating circumstances.

This disclosure relates to tissue closure devices, including surgical suturing devices as well as such devices that can be used for intra-abdominal suturing and suturing of puncture wounds generated by surgical trocars and other puncturing devices.

SUMMARY

A sliding suture grasping device may be used to cross a tissue bed and retrieve a suture by initially capturing a portion of the suture disposed within the body cavity and then facilitating free movement or sliding of the suture at or within the device tip during retraction of the device from the body cavity.

The sliding suture grasper may combine a needle with a means to retrieve suture from a template used to guide the insertion and retrieval procedure. For example, the sliding suture grasper may be inserted into an insertion point on the proximal portion of the template transverse to the centerline of the template from an exit point on the template body to guide the grasper through the soft tissue and toward a suture portion retained by a distal part of the template for capture and retrieval of the suture portion. This retrieval maneuver could then be repeated on an opposite side of the template to facilitate retrieval of the other end of the suture on the opposite side of an opening in the tissue bed, for example.

The suture grasper may comprise at least one element that can expand laterally to encircle the suture and that is configured to allow suture to slide freely after the suture has been captured.

The grasper may including a keying feature on the proximal handle that interacts with a keyway on the proximal end of the template. The key and keyway could be configured such that the lateral expanding element is generally orthogonal to the suture to be captured held in the template when the key resides in the keyway. The key/keyway feature could act as a stop and limit the penetration distance of the needle.

The suture grasper may be configured to automatically activate to expand when approaching the suture target and to deactivate or close when retracting the retriever thereby capturing the suture during the retraction maneuver.

In one exemplary aspect, a suture grasper includes an elongated tubular body defining an inner lumen, the elongated tubular body having a proximal end and a distal end. The suture grasper further includes a handle attached to the proximal end of the elongated tubular element; an inner member element slidably disposed within the lumen of the elongated tubular body, the inner member element having a proximal end configured to slidably extend from and retract into the handle, and having a distal end configured with at least one grasping element; a push button extending from a proximal end of the handle, the push button being coupled to the inner member element for actuation or movement of the inner member element in a distal direction or a proximal direction. The suture grasper includes a proximal spring disposed within the push button, the proximal spring abutting against the proximal end of the inner member element, to bias the inner member element distally. The suture grasper also includes an intermediate spring for biasing the push button and the inner member element in the proximal direction. The suture grasper further includes a distal spring disposed between a distal end of the handle and a flanged proximal end of the elongated tubular body, the push button including a distal end for contacting the flanged proximal end. In one aspect, actuation of the push button in the distal direction beyond a predetermined point after compression of the intermediate spring causes the distal end of the push button to compress the distal spring via the flanged proximal end, and the flanged proximal end transfers force to actuate the tubular body distally relative to the inner member element, to actuate and close the at least one grasping element.

In one aspect, the at least one grasping element is configured to expand wider than the elongated tubular body.

In one aspect, the at least one grasping element includes at least two expandable arms.

In one aspect, the at least two expandable arms expand as the at least one grasping element is extended beyond the distal end of the elongated tubular body. The at least two expandable arms include a left arm and a right arm, the left arm and the right arm having a different hinge point. The left arm and the right arm extend radially away at different distances.

In one aspect, the at least one grasping element includes at least two expandable arms, and the at least two expandable arms expand as the at least one grasping element is extended beyond the distal end of the elongated tubular body.

In one aspect, the distal spring biases the push button and the inner member element in the proximal direction. The push button includes a detent end, and the distal spring biases the detent end to rest against an inner proximal wall of the handle when the push button is in a released position. The detent end of the push button compresses the distal spring when the push button is depressed, and compression of the distal spring transfers force to actuate the inner member element in the distal direction.

In one aspect, a distal end of the push button compresses the intermediate spring when the push button is depressed, and compression of the intermediate spring transfers force to actuate the inner member element in the distal direction.

In one aspect, the proximal end of the inner member element includes a side post, and the handle includes a stop element, the stop limiting travel of the elongated tubular body in the proximal direction via abutment with the flanged proximal end, and the stop element limiting travel of the inner member element in the distal direction via abutment with the side post. The handle includes an inner proximal wall, the inner proximal wall limiting travel of the inner member element in the proximal direction via abutment with the side post.

In one aspect, the suture grasper further comprises a locking member to retain the push button in a predetermined axial location. The locking member extends laterally outward with respect to an axial direction of the push button.

In one aspect, the distal end of the elongated tubular body includes a sharp tip capable of crossing or penetrating tissue. The sharp tip of the distal end of the elongated tubular body is beveled and configured to cross or penetrate tissue. The at least one grasping element includes at least two expandable arms, and each of the at least two expandable arms have a different radius of curvature when expanding radially.

BRIEF DESCRIPTION OF THE DRAWINGS

The accompanying drawings, which are incorporated in and constitute a part of this specification, illustrate various embodiments consistent with the invention, and, together with the description, serve to explain the principles of the invention.

FIG. 9 is a side view of a sliding suture grasper, in accordance with other aspects of the present invention;

FIG. 10 is a front sectional view of the sliding suture grasper of FIG. 9 at A-A.

DETAILED DESCRIPTION

Figure 2:
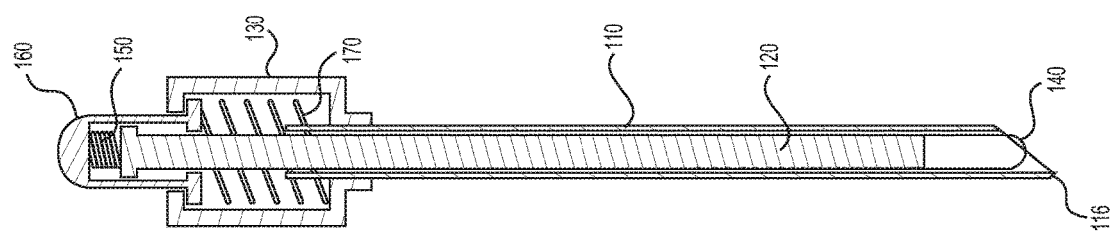
FIG. 2 is a side sectional view showing the sliding suture grasper of FIG. 1 in a certain state of use, in accordance with certain aspects of the present invention.

The invention will now be described with reference to the drawing figures, in which like reference numerals refer to like parts throughout.

Various aspects of a sliding suture grasping device may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations of a sliding suture grasping device in addition to the orientation depicted in the drawings. By way of example, if aspects of a sliding suture grasping device shown in the drawings are turned over, elements described as being on the "bottom" side of the other elements would then be oriented on the "top" side of the other elements. The term "bottom" can therefore encompass both an orientation of "bottom" and "top" depending on the particular orientation of the apparatus.

As shown in FIGS. 1-4, a sliding suture grasper device 100 is comprised of an elongated tubular body 110 having a proximal end 112 and a distal end 114. The distal end 114 may be beveled to provide a sharp tip 116 capable of crossing or penetrating tissue. Within the lumen of the elongated tubular body 110 resides an inner member element 120 having a proximal end 122 and distal end 124 that is free to move along the length of the elongated tubular body 110. The elongated tubular body 110 may be attached to a handle 130 such that the proximal end 122 of the inner member element 120 may slidably extend from and retract into the handle 130. The distal end 124 of the inner member element 120 may comprise at least one grasping element 140 that expands wider than the elongated tubular body 110 diameter when the grasping element 140 is extended distal of the elongated tubular body 110. The proximal end 122 of the inner member element 120 rests against a proximal spring 150 that resides within a push button 160. The push button 160 resides within the proximal end of the handle 130 and can be actuated by pushing in the distal direction to advance the inner member element 120 distally allowing the grasping element 140 to expand. Within the handle 130 and distal to the push button 160 resides a distal spring 170 that biases the push button 160 in the proximal direction against the proximal end of the handle 130 and also biases the inner member element 120 in the proximal direction.

Figure 1:
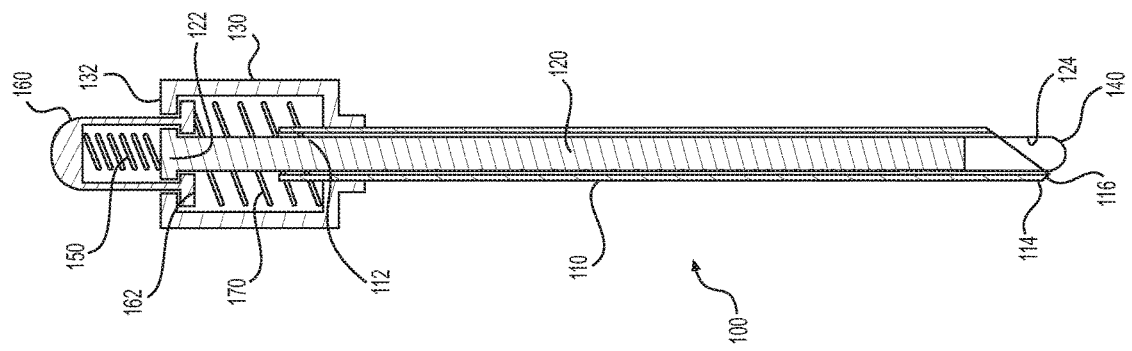
FIG. 1 is a side sectional view of a sliding suture grasper, in accordance with certain aspects of the present invention.

As shown in FIG. 2, during use, the grasper device 100 may be inserted into a tissue bed. When doing so, the inner member element 120 may be pushed proximally due to tissue resistance thereby compressing the proximal spring 150 much like a traditional Veress needle. In this manner, the grasping element 140 may be configured with at least two expandable arms 142 (see FIG. 3) that form a bulbous, rounded distal end when not in the expanded grasping position. The grasping element 140 may thus provide a degree of safety against an accidental poke from the sharp tip 116 by providing a rounded distal end Which extends beyond the sharp tip 116, as shown in FIG. 1. The inner member element 120 may be pushed proximally until the grasping element 140 no longer extends beyond the distal tip 116, allowing the distal tip 116 to penetrate the tissue bed.

As the distal tip 116 of the device exits the tissue into a body cavity, for example, the pressure against the grasping element 140 is relieved and the inner member element 120 returns to its resting state wherein a detent end 162 of the push button 160 rests against a proximal wall 132 of the handle 130, as shown in FIG. 1. The device 100 may thus be positioned in proximity to a portion of suture 180 to be captured.

Figure 4:
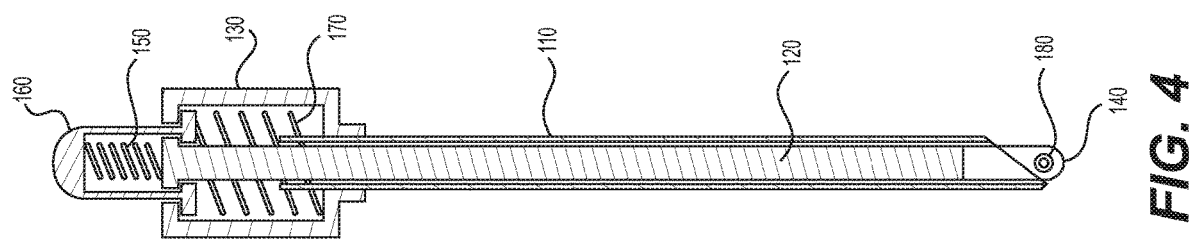
FIG. 4 is a side sectional view showing the sliding suture grasper of FIG. 1 in another state of use including a captured portion of a suture, in accordance with certain aspects of the present invention.
Figure 3:
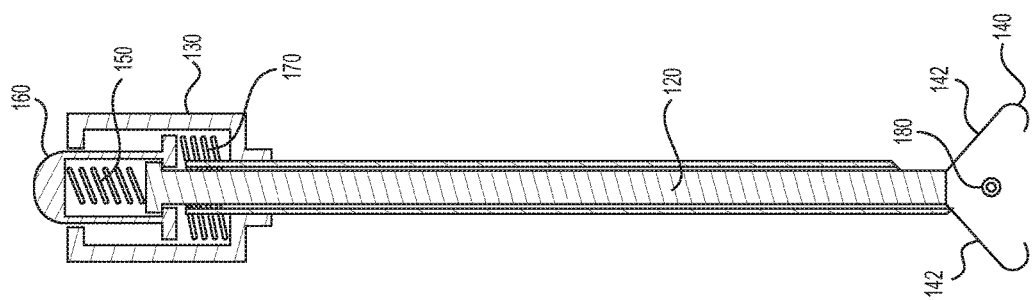
FIG. 3 is a side sectional view showing the sliding suture grasper of FIG. 1 in another state of use, in accordance with certain aspects of the present invention.

As shown in FIG. 3, with the device 100 thus positioned near the suture 180, the push button 160 may then be depressed to compress the distal spring 170 with the detent end 162 of the push button 160. The compression of the distal spring 170 in turn transfers force to the inner member element 120 to thereby actuate the inner member element 120 in the distal direction. The expandable arms 142 of the grasping element 140, which may be spring actuated by being comprised of a suitable material formed to maintain a certain shape, may expand upon being released from the distal end 114 of the elongated tubular body 110. As shown in FIG. 4, upon release of the push button 160, the distal spring 170 drives the push button 160 proximally until the detent end 162 of the push button 160 seats against the proximal wall 132 of the handle 130. As the distal spring 170 drives the push button 160 proximally, the inner member 120 may be actuated in the proximal direction causing the expandable arms 142 to close around the suture portion 180.

At this time, the at least one grasping element 140 has captured and secured the portion of suture 180 in its proximity within or near the distal tip 116 of the device 100. The grasping element 140 is configured to secure the suture portion 180 in a manner that allows it to slide freely through the grasping element 140 upon retraction of the device 100 from the body cavity.

FIGS. 5-8 illustrate a sliding suture grasper device 200 in accordance with yet other aspects of the present disclosure. The device 200 may be used to cross a tissue bed and retrieve a suture by initially capturing a portion of the suture disposed within a body cavity and then facilitating free movement or sliding of the suture at or within the device tip during retraction of the device from the body cavity. The sliding grasper device 200 employs a means to position nearby the suture, expand or open a grasping element 140 about the suture, and then capture and retain the suture as part of a continuous action of a push button system.

As shown in FIGS. 5-8, the grasper device 200 may comprise an elongated tubular body 210 having a proximal end 212 and distal end 214, an inner member element 220 having a proximal end 222, a distal end 224, and featuring a grasping element 240 at its distal end 224, a handle 230, a proximal spring 250, a mid spring 255, a push button 260, and a distal spring 270. The elongated tubular body 210 includes a distal end 214 beveled to provide a sharp tip 216 capable of crossing or penetrating tissue. The proximal end 212 of the elongated tubular body 210 may be flanged and/or configured for slidably mounting within a distal portion 232 of the handle 230. The elongate tubular body 210 is free to move a predetermined distance within the distal portion 230 of the handle 230 and has a stroke that is limited by the interaction of the proximal end 212 with features within the handle 230, such as a stop element 234.

The elongate tubular body 210 may be biased in the proximal direction by inclusion of the distal spring 270 positioned between the proximal end 222 of the elongate tubular body 210 and the handle 230. Within the lumen of the elongated tubular body 210 slidably resides the inner member element 220 having proximal end 222 and distal end 224, the inner member element 220 being free to move along the longitudinal length of the elongated tubular body 210. The proximal end 222 of the inner member element 220 may also be flanged and include a side post 223 distal to the flanged end 222. The flanged proximal end 222 of the inner member element 220 maintains and secures the inner member element 220 within the inner core of the push button 260.

The distal end of the inner member element comprises at least one grasping element 240 that may include one or more expandable arms 242, for example. The expandable arms 242 of the grasping element 240 may be spring actuated by being comprised of a suitable material formed to maintain a certain shape, and may be configured to expand upon being released from the distal end 214 of the elongated tubular body 210. The expandable arms 242 may expand wider than a diameter of the elongated tubular body 210 when the grasping element 240 is extended distal to the distal end 214 of the tubular body 210. Because the distal end 214 of the tubular body 210 may be beveled, in accordance with aspects of the present disclosure, each arm 242 of the grasping element 240 may have a different radius of curvature to prevent one arm from expanding radially further due to the different distances each arm 242 will extend from the beveled end 214. For example, in a configuration wherein the arms 242 do not share a common hinge point, a left arm and a right arm will extend radially away different distances due to one arm having a cantilevered length that is greater than the cantilevered length of the second arm due to an effective hinge point formed by the beveled end 214 being different for the first arm than the second arm. By having a different radius of curvature, for example, permits both arms 242 to open approximately symmetrically about a longitudinal centerline of the device 200.

The proximal spring 250 is situated proximal to the flanged end 222 of the inner element and within the inner core of the push button 260 as a means to bias the inner member element 220 towards the distal end of the push button 260. The proximal spring 250 may comprise a single spring of a known constant spring rate, a single spring with variable spring rates along its length, or multiple springs with varying spring rates. These multiple springs could be preferably arranged in tandem versus coaxial or parallel. The side post 223 on the inner member element 220 limits the longitudinal movement or stroke of the inner member in both the proximal and distal directions within the handle 230. For example, the side post 223 may be formed to abut against a proximal end 236 of the handle 230 at one limiting end of the inner member stroke and to abut against the same stop element 234 formed to seat the proximal end 212 of the elongated tubular body 210. In accordance with other aspects of the present disclosure, the stop element 234 may be separated into multiple detents for limiting the separate strokes of the elongated tubular member 210 and the inner member element 220.

The mid spring 255 may be configured to seat against an extended distal end 262 of the push button 260 and bias the push button 260 in the proximal direction. The push button 260 may thus be positioned against a push button detent 238 configured into the proximal wall 236 of the handle 230 when the mid spring 255 is extended. A distal end 256 of the mid spring 255 may seat against an inner flange 237 configured into the stop 234 or any suitable portion of the handle 230 that is isolated from the elongate tubular body 210 and distal spring 270.

The push button 260 resides within the proximal end of the handle 230 and is actuated by pushing in the distal direction to advance the inner member element 220 distally which allows the grasping element 240 to expand. The push button 260 may include side openings or slots designed to allow unconstrained, longitudinal movement of the side post 223 of the inner member element 220.

Figures 5, 6:
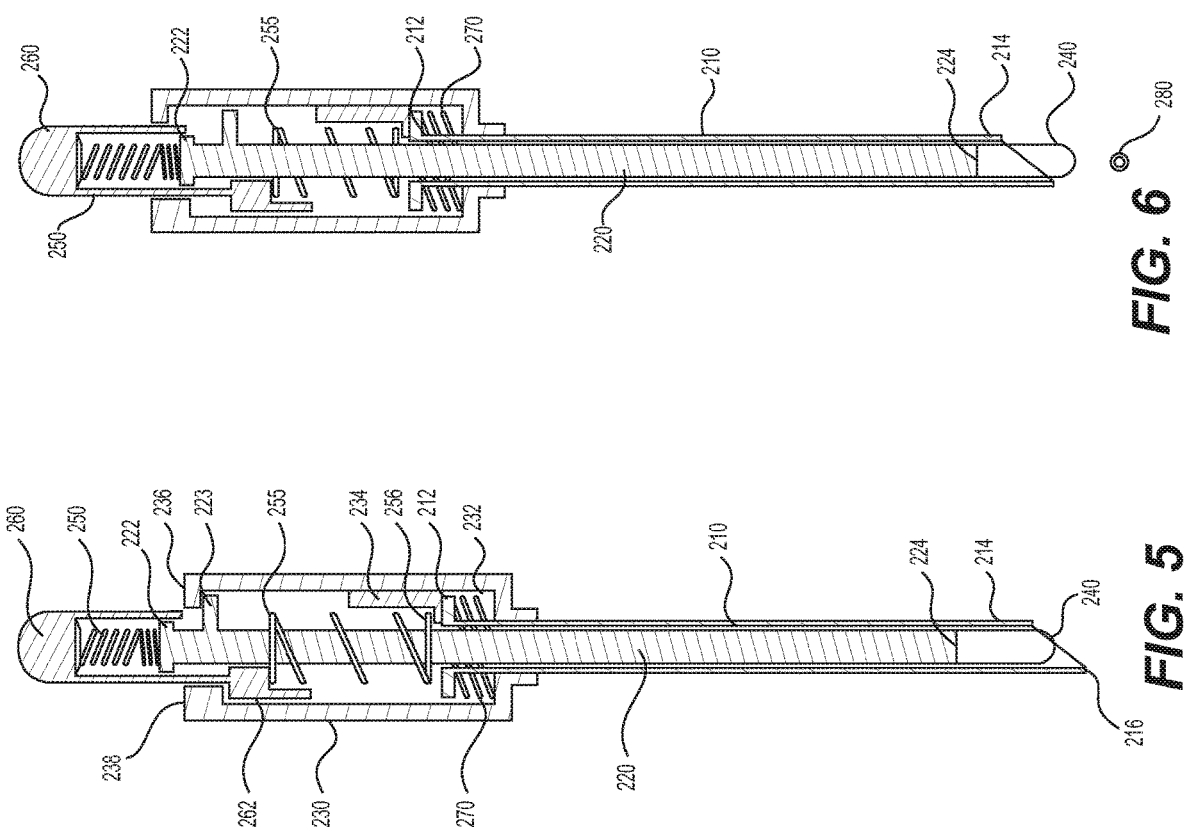
FIG. 5 is a side sectional view of a sliding suture grasper, in accordance with other aspects of the present invention.
FIG. 6 is a side sectional view showing the sliding suture grasper of FIG. 5 in a certain state of use, in accordance with certain aspects of the present invention.

In use, as shown in FIGS. 5-8, the device 200 may first be introduced into a template for guiding the device 200 in a predetermined direction toward a tissue bed. As shown in FIG. 5, when the device 200 is inserted into the tissue bed, the inner member element 220 may be pushed proximally due to tissue resistance on the bulbous, rounded end of the grasping element 240 formed when the two arms 242 are compressed in a clamping fashion toward each other. As the inner member element 220 is pushed proximally, the proximal spring 250 may be compressed and/or the mid spring 255 may be stretched such that the inner member element 220 retracts into the elongated tubular body 210 to expose the sharp, beveled tip 216 for penetration through the tissue bed, much like a traditional Veress needle. As the distal tip 216 of the device 200 then exits the tissue bed into the body cavity, the resistance is relieved and the inner member element 220 returns to its resting state. The depth of penetration may be limited by the interference of the handle 230 with a proximal portion of the template thereby positioning the distal end of the device 200 above and in close proximity to a portion of suture 280 to be captured. The push button 260 is then actuated to sequentially compress the proximal springs 250, the mid spring 255 and finally the distal spring 270.

Figure 7:
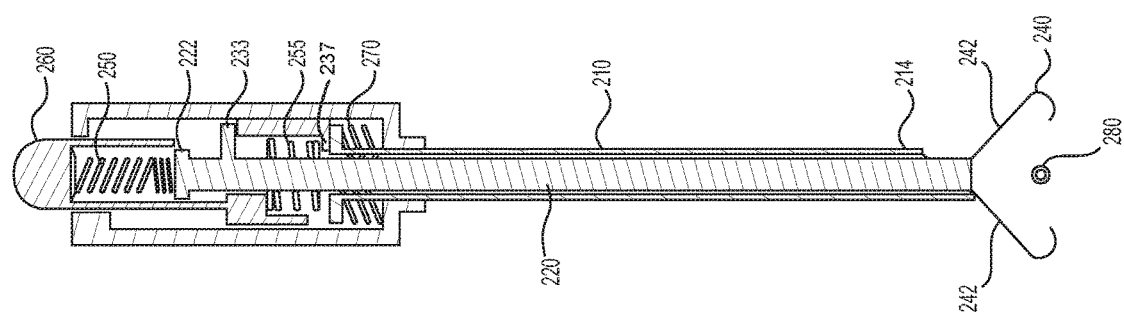
FIG. 7 is a side sectional view showing the sliding suture grasper of FIG. 5 in another state of use, in accordance with certain aspects of the present invention.
Figure 12:
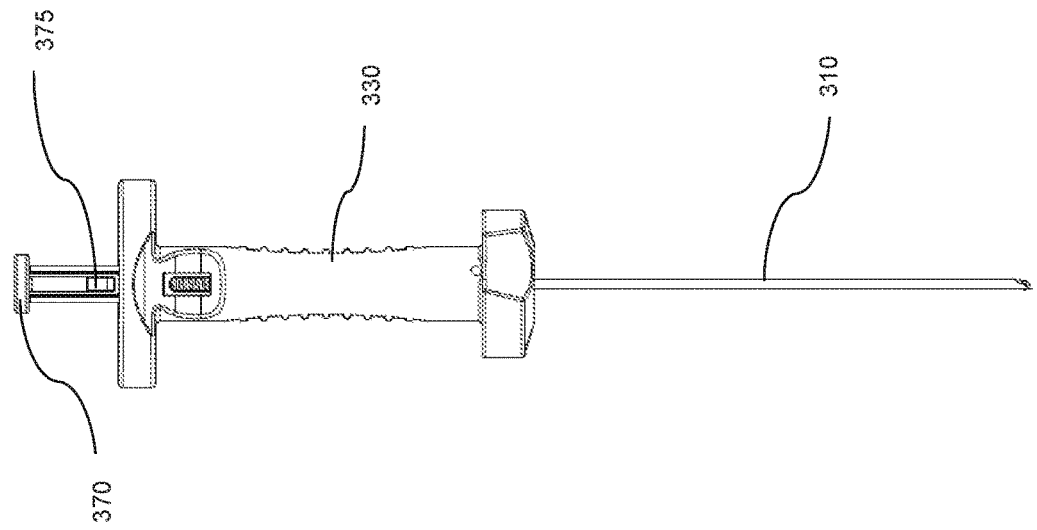
FIG. 12 is a front view of a sliding suture grasper in accordance with certain aspects of the present disclosure in another state of use.
Figure 11:
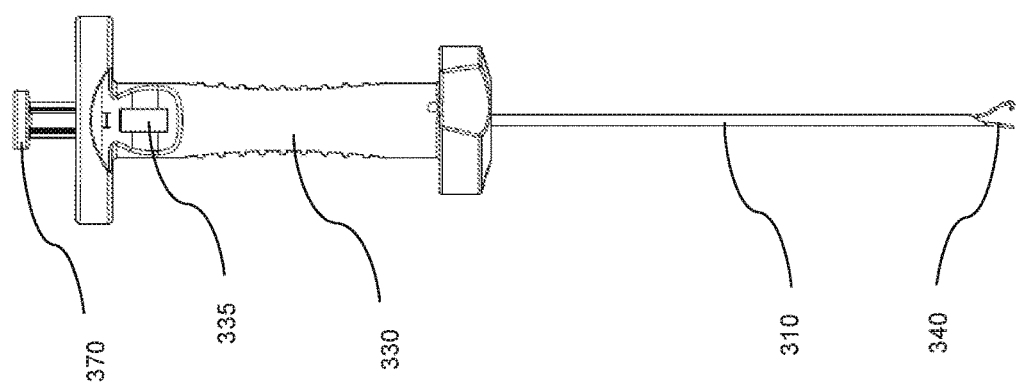
FIG. 11 is a front view of a sliding suture grasper in accordance with certain aspects of the present disclosure in a certain state of use.

As shown in FIGS. 6 and 7, actuation of the push button 260 in the distal direction initially moves the inner member element 220 distally until the side post 223 abuts against the stop 234 configured into the handle 230. At this point, the expandable arms 242 of the grasper element 240 may extend beyond the distal end 214 of the tubular body 210 such that the arms 242 are extended toward and opened radially around the suture portion 280. With the side post 223 abutting the stop 234, the inner member element 220 is prevented from any further longitudinal movement in the distal direction with respect to the handle 230.

Figure 8:
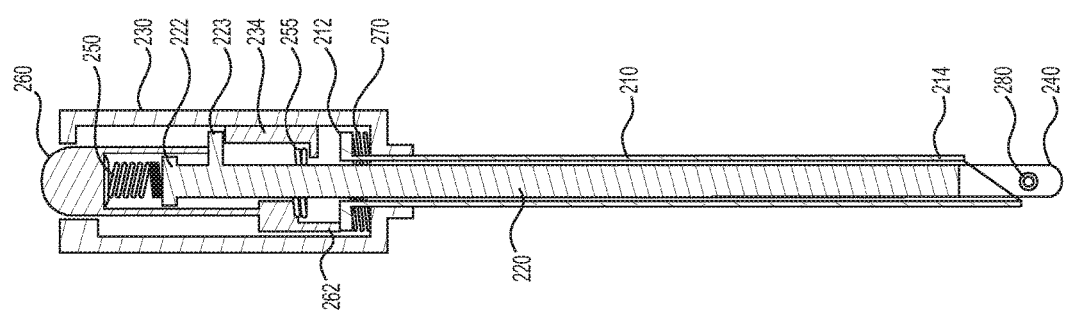
FIG. 8 is a side sectional view showing the sliding suture grasper of FIG. 5 in another state of use including a captured portion of a suture, in accordance with certain aspects of the present invention.

Rather, as shown in FIG. 8, continued actuation of the push button 260 forces the distal end 262 of the push button 260 to abut the flanged proximal end 212 of the elongated tubular body 210. The proximal spring 250, the mid spring 255, and the distal spring 270 are all compressed as the distal end 262 of the push button 260 pushes the elongated tubular body 210 distally. As the distal end 214 of the tubular member 210 slides over the expanded arms 242 of the grasping element 240, the expanded arms 242 are forced to close around the suture portion 280 in order to slidably capture the suture. The push button 260 could be held manually by the surgeon or alternatively may comprise a locking feature, as will be described in detail below, to maintain the security of grasping element 240 in a closed position with the suture secured in a sliding embrace therein. The device 200 would then be withdrawn outside of the body cavity until the end of the suture completely exits the device 200. Upon release of the push button 260 and/or lock, the various springs would return to their extended positions and be ready for the next suture retrieval maneuver.

FIGS. 9-12 illustrate a sliding suture grasper device 300 in accordance with yet another aspect of the present disclosure. The device 300 may comprise an elongated tubular body 310 having a proximal end 312 and distal end 314, and an inner member element 320 having a proximal end 322 and a distal end 324, the distal end 324 featuring a grasping element 340. In one aspect, the device 300 may include a handle 330, a proximal spring 350, a mid spring 355, a distal spring 360, and a push button 370. In one aspect, the push button 370 may include a locking member 375, which may be biased to extend laterally outward with respect to an axial direction of the push button 370. In one aspect, the handle 330 may include an opening 335 to secure the locking member 375 such that the push button 370 is retained at a predetermined axial location. In one aspect, securing the push button 370 at the predetermined axial location maintains the grasping element 340 in a closed position with a suture secured in a sliding embrace therein.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

What is claimed is:

1. An instrument comprising:
   an elongated body defining a lumen, the elongated body having a proximal portion and a distal portion;
   a handle attached to the proximal portion of the elongated body;
   an inner member slidably disposed within the lumen of the elongated body, the inner member having a distal end effector;
   a push button extending from a proximal portion of the handle, the push button configured to actuate or move the inner member;
   a first spring disposed between a portion of the push button and a portion of the inner member, the first spring being configured to bias the inner member in a distal direction; and
   a second spring configured to bias the push button and the inner member in a proximal direction.

2. The instrument of claim 1, wherein the first spring is configured to compress when the distal end effector is pushed into the elongated body, and the second spring is configured to compress when the push button is pushed distally to advance the distal end effector out of the elongated body.

3. The instrument of claim 1, wherein the second spring engages the push button.

4. The instrument of claim 3, wherein the second spring engages a distal portion of the push button.

5. The instrument of claim 1, wherein the second spring is disposed around the inner member.

6. The instrument of claim 1, wherein the second spring biases the push button against a proximal portion of the handle.

7. The instrument of claim 1, wherein the first spring is disposed in the push button.

8. The instrument of claim 1, wherein the distal end effector includes at least one grasping element.

9. The instrument of claim 8, wherein the at least one grasping element is configured to expand when in an extended configuration beyond the distal portion of the elongated body.

10. The instrument of claim 9, wherein the at least one grasping element includes at least two expandable arms.

11. The instrument of claim 1, wherein the distal end effector has a round distal portion when in a retracted configuration.

12. The instrument of claim 1, wherein the distal portion of the elongated body includes a sharp tip.

13. The instrument of claim 1, wherein the first spring engages the push button.

14. The instrument of claim 1, wherein the push button has a detent portion that rests against a proximal wall of the handle in a resting state.

15. The instrument of claim 1, wherein a proximal portion of the inner member is received in the push button.

16. The instrument of claim 1, further comprising a stop element, wherein the second spring extends between the stop element and the portion of the push button.

17. The instrument of claim 1, further comprising a third spring configured to bias the elongated body in the proximal direction, wherein the third spring extends between a flange of the elongated body and a distal portion of the handle.

18. The instrument of claim 1, wherein the push button has a locking member, and the handle has an opening configured to secure the locking member and to retain the push button in a predetermined axial location.

19. The instrument of claim 18, wherein the locking member extends from the push button in a lateral direction with respect to an axial direction of the push button.

20. The instrument of claim 19, wherein the locking member is biased in the lateral direction.

* * * * *